US008389761B2

(12) United States Patent
Dumesic et al.

(10) Patent No.: US 8,389,761 B2
(45) Date of Patent: Mar. 5, 2013

(54) METHOD TO PRODUCE AND RECOVER LEVULINIC ACID AND/OR GAMMA-VALEROLACTONE FROM AQUEOUS SOLUTIONS USING ALKYLPHENOLS

(75) Inventors: James Dumesic, Verona, WI (US); Jesse Bond, Madison, WI (US); David Alonso, Madison, WI (US); Thatcher Root, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 68 days.

(21) Appl. No.: 13/115,420

(22) Filed: May 25, 2011

(65) Prior Publication Data

US 2012/0302764 A1 Nov. 29, 2012

(51) Int. Cl.
C07C 59/185 (2006.01)
C07C 51/48 (2006.01)
C07D 307/33 (2006.01)
(52) U.S. Cl. .................. 562/577; 549/326; 562/515
(58) Field of Classification Search .................. 562/515, 562/577; 549/326
See application file for complete search history.

(56) References Cited

U.S. PATENT DOCUMENTS

| 5,608,105 A | 3/1997 | Fitzpatrick |
| 2010/0312006 A1 | 12/2010 | Lake et al. |

FOREIGN PATENT DOCUMENTS

| JP | 3337326 A | 10/2002 |
| WO | WO 2009/130386 A1 | 10/2009 |

OTHER PUBLICATIONS

Alonso et al., Catalytic conversion of biomass to biofuels, *Green Chem.* 12 , 1493-1513 (2010).
Bond et al., Integrated Catalytic Conversion of γ-Valerolactone to Liquid Alkenes for Transportation Fuels, *Science* 327 , 1110-1114 (2010).
Bozell et al., Production of levulinic acid and use as a platform chemical for derived products, *Resour. Conserv. Recy.* 28 , 227-239 (2000).
Bozell et al., Technology development for the production of biobased products from biorefinery carbohydrates—the US Department of Energy's "Top 10" revisited, *Green Chem.* 12 , 539-554 (2010).
Bozell, J.J., Connecting Biomass and Petroleum Processing with a Chemical Bridge, *Science* 329, 522-523 (2010).
Braden, D.J., Thesis—Catalytic conversion of Lignocellulosic Biomass into Liquid Transportation Fuels: Fundamental and Applied Approaches, UW-Madison (2010).
Deng et al., Catalytic Conversion of Biomass-Derived Carbohydrates into γ-Valerolactone without Using an External $H_2$ Supply, *Angew. Chem. Int. Ed.* 48, 6529-6532 (2009).
Fegyverneki et al., Gamma-valerolactone-based solvents, *Tetrahedron* 66, 1078-1081 (2010).
Fellay et al., A Viable Hydrogen-Storage System Based on Selective Formic Acid Decomposition with a Ruthenium Catalyst, *Agnew. Chem. Int. Edit.* 47, 3966-3968 (2008).
Geilen et al., Selective and Flexible Transformation of Biomass-Derived Platform Chemicals by a Multifunctional Catalytic System, *Angew. Chem. Inter. Ed.* 49, 5510-5514 (2010).
Heeres et al., Combined dehydration/(transfer)-hydrogenation of C6-sugars (D-glucose and D-fructose) to γ-valerolactone using ruthenium catalysts, *Green Chem.* 11, 1247-1255 (2009).
Horvat et al., Mechanism of Levulinic Acid Formation, *Tetrahedron Lett.* 26, No. 17, 2111-2114 (1985).
Horvath et al., γ-Valerolactone—a sustainable liquid for energy and carbon-based chemicals, *Green Chem.* 10, 238-242 (2008).
Huber et al., Raney Ni-Sn Catalyst for $H_2$ Production from Biomass-Derived Hydrocarbons, *Science* 300, 2075-2077 (2003).
Kirk-Othmer Encyclopedia of Chemical Technology (Ed Wiley, New York 2000), Alkylphenols, vol. 2, pp. 203-232.
Kunkes et al., Catalytic Conversion of Biomass to Monofunctional Hydrocarbons and Targeted Liquid-fuel Classes, *Science* 322, 417-421 (2008).
Lange et al., Towards "bio-based" Nylon: conversion of γ-valerolactone to methyl pentenoate under catalytic distillation conditions, *Chem. Commun.*, 3488-3490 (2007).
Lange et al., Valeric Biofuels: A Platform of Cellulosic Transportation Fuels, *Angew. Chem. Inter. Ed.* 49, 4479-4483 (2010).
Liu et al., The Effect if Flow Rate of Compressed Hot Water on Xylan, Lignin, and Total Mass Removal from Corn Stover, *Ind. Eng. Chem. Resear.* 42, 5409-5416 (2003).
Mehdi et al., Integration of Homogeneous and Heterogeneous Catalytic Processes for a Multi-step Conversion of Biomass: From Sucrose to Levulinic Acid, γ-Valerolactone, 1,4-Pentanediol, 2-methyl-tetrahydrofuran, and Alkanes, *Top. Catal.* 48, 49-54 ( 2008).
Prairie et al., A Fourier Transform Infrared Spectroscopic Study of $CO_2$ Methanation on Supported Ruthenium, *J. Catal.* 129, 130-144 (1991).
Riguetto et al., Ru-Sn catalysts for selective hydrogenation of crontonaldehyde: Effect of the Sn/(Ru + Sn) ratio, *Appl .Catal. Gen.* 318, 70-78 (2007).
Serrano-Ruiz et al., Conversion of cellulose to hydrocarbon fuels by progressive removal of oxygen, *Appl. Catal. B-Environ.* 100, 184-189 (2010).
Springerova et al., Selective hydrogenation of α,β-unsaturated carbonyl compounds on supported Ru-Sn catalysts, *Res. Chem. Intermediat.* 31, 785-795 (2005).
Yan et al., Synthesis of γ-Valerolactone by Hydrogenation of Biomass-derived Levulinic Acid over Ru/C Catalyst, *Energ. fuel* 23, 3853-3858 (2009).
Alonso, David Martin, et al., "Production of Biofuels from Cellulose and Corn Stover Using Alkylphenol Solvents," Chemsuschem, vol. 4, No. 8, pp. 1078-1081, Aug. 22, 2011.
Gurbuz, Elif I., et al., "Conversion of Hemicellulose to Furfural and Levulinic Acid using Biphasic Reactors with Alkylphenol Solvents," Chemsuschem, vol. 5, No. 2, pp. 383-387, Feb. 13, 2012.

*Primary Examiner* — Bernard Dentz

(74) *Attorney, Agent, or Firm* — Joseph T. Leone, Esq.; DeWitt Ross & Stevens S.C.

(57) ABSTRACT

A method to produce levulinic acid (LA) and γ-valerolactone (GVL) from biomass-derived cellulose by selective extraction of LA by alkylphenol (AP) and hydrogenation of LA, in which mineral acid used in the method is recycled and the final concentration of GVL is increased by successive extraction/hydrogenation steps to allow for effective separation by distillation.

25 Claims, 9 Drawing Sheets

METHOD TO PRODUCE AND RECOVER LEVULINIC ACID AND/OR GAMMA-VALEROLACTONE FROM AQUEOUS SOLUTIONS USING ALKYLPHENOLS

FEDERAL FUNDING STATEMENT

This invention was made with government support under W911NF-09-0010 awarded by the ARMY/ARO. The government has certain rights in the invention.

BACKGROUND

Significant advances have been made in recent years with respect to using heterogeneous catalysts for converting biomass-derived compounds to fuels and chemicals. Conventional approaches deconstruct solid cellulose into smaller molecules that are soluble in various solvents (e.g., water, ionic liquids), thereby allowing transport of these reactants to the active sites on the heterogeneous catalyst, the majority of which are located within the pores of a high-surface area material. A difficulty in implementing this strategy is that chemical components used to deconstruct solid cellulose (e.g., sulfuric acid) may alter the performance of heterogeneous catalysts used subsequently to convert the soluble biomass-derived reactants to the desired fuels and/or chemicals. As a result, costly purification steps are required to implement a cascade catalytic process. Thus, the present method addresses a long-felt and unmet need by providing a route to levulinic acid and γ-valerolactone that uses an extraction solvent that does not entrain the strong acid used to deconstruct the reactant cellulose.

SUMMARY OF THE INVENTION

Making fuels and chemicals from biomass is complicated by the need to separate and to purify the intermediate platform molecules at high yields. Conventional approaches to making useful chemicals from biomass typically require very difficult and economically unfeasible separation and purification steps. Disclosed herein is a method in which levulinic acid (LA) is first produced from biomass (e.g., corn stover) by cellulose deconstruction. The LA so formed is then extracted from the aqueous phase using one or more alkylphenol (AP) solvents. The LA so formed is a value-added, platform compound that finds commercial use as an intermediate or reactant in a host of industrially useful processes. Additionally, the LA may optionally be hydrogenated to γ-valerolactone (GVL). This strategy allows for any acid that may be used in the process (preferably sulfuric acid) to be recycled very nearly completely (>99%).

Thus, disclosed and claimed herein is a method to make and extract levulinic acid (LA) from aqueous solutions. The method comprises acid catalyzed deconstruction of biomass in an aqueous solution to yield LA. The LA is then extracted from the aqueous solution using an extraction solvent comprising at least one alkylphenol (AP).

Preferably, the aqueous solution used to deconstruct the biomass comprises a mineral, organic or solid acid, such as hydrochloric acid, nitric acid, phosphoric acid, sulfuric acid, boric acid, hydrofluoric acid, hydrobromic acid, acetic acid, oxalic acid, sulfonic acid, triflouroacetic acid, sulfated zirconia, zeolites, ion exchange resins and/or heteropolyacids, or high temperature water. The AP extraction solvent is preferably selected from the group consisting of

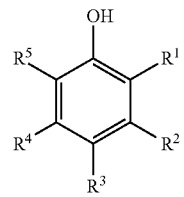

wherein $R^1$-$R^5$ are independently selected from the group consisting of hydrogen, hydroxyl, esters, ethers, carboxylic acids, and $C_1$-$C_{24}$ linear, branched, or cyclic alkyl and alkene, provided that at least one of $R^1$-$R^5$ is alkyl.

The LA formed by the method can be separated from the AP solvent (by distillation or any other means) or processed together in the AP to produce derivatives, such as GVL by hydrogenation. Hydrogenating the LA into GVL can be accomplished in a number of ways. Preferably the hydrogenation takes place in the presence of a catalyst comprising one or more metals from Groups 6-14 of the periodic table, more preferably still a catalyst comprising ruthenium, nickel, platinum, palladium, rhodium, tin, copper, chromium and combinations thereof, and most preferably a catalyst comprising ruthenium and tin. The hydrogenation of LA to GVL may also be accomplished by hydrogen transfer using homogeneous or solid oxide catalysts in the presence of an H-donor, such as an alcohol. In transfer hydrogenation, higher yields can be achieved by first converting the LA into a LA ester (by acid catalyzed reaction with an alcohol or an olefin) and then reducing the LA ester to GVL by transfer hydrogenation. Preferably, the LA ester is reduced to GVL in the presence of a solid oxide catalyst.

Thus the entire route to yield GVL proceeds by deconstructing biomass in an aqueous solution using an acid catalyst (homogeneous or heterogeneous) to yield LA, extracting the LA from the aqueous solution using an extraction solvent comprising at least one AP, and hydrogenating the LA into GVL.

A distinct advantage of the method is that the GVL product is stable during the hydrogenation of LA. Thus, it is possible to increase the GVL concentration in the product mix by successive cycles of cellulose deconstruction, LA extraction, and LA hydrogenation to GVL. By accumulating a large concentration of GVL in the product mix, GVL can be easily (and cost-effectively) separated from the AP solvent by simple distillation.

The overall strategy disclosed herein is to convert lignocellulosic biomass to value-added fuels and chemicals by partially removing oxygen to yield reactive intermediates (denoted herein as platform molecules, such as LA, GVL, and others). The platform molecules are valuable and useful commercial products. The platform molecules can be converted into any number of desired final products, including liquid transportation fuels. As a general proposition, platform molecules have fewer functional groups as compared to the carbohydrates found naturally in biomass (e.g., xylose, glucose). Because there are less reactive functional groups, the platform molecules can be selectively upgraded to other useful chemicals via catalytic upgrading processes.

Another advantage of this strategy is that the lower degrees of functionality and boiling points of these platform molecules allow for catalytic processing in the vapor phase and/or in organic solvents. This alleviates the need to develop heterogeneous catalysts that are stable under more demanding hydro-thermal reaction conditions. One such platform molecule is levulinic acid (LA) (3, 4) from which a variety of fuels and chemicals can be made, such as valeric acid esters (5), methyltetrahydrofuran (6-8), and esters and ketals of LA (9). Another building block from the reduction of LA is γ-valerolactone (GVL) (10, 11), which can be used directly as a fuel additive (12), or as a precursor for fuels (13) and chemicals (14, 15). While LA can be formed in significant yields (>50%) by cellulose deconstruction in aqueous solutions of mineral acids such as sulfuric acid (SA) (16, 17), a challenge for profitable, large-scale production of LA and its derivatives has been separating the LA from the mineral acid used in the process. This is necessary so that the LA can be further processed downstream without the negative effects of the mineral acid (18).

In the present method, alkylphenol (AP) solvents (19) are used as a partitioning agent in a method to produce LA and/or GVL from biomass in general, and lignocellulosic biomass in particular. As illustrated schematically in FIG. 1, AP solvents can be used to selectively extract LA from aqueous solutions after a cellulose deconstruction step. In addition, AP solvents extract GVL from water with a higher partition coefficient (the concentration of the solute in the organic phase divided by the concentration of the solute in the aqueous phase) compared to LA. Accordingly, the GVL concentration in the AP solvent can be increased by the conversion of LA to GVL, combined with the recycle of this stream for successive extractions. Importantly, a preferred carbon-supported RuSn catalyst (20, 21) can be used to selectively reduce LA to GVL by hydrogenation in the presence of AP, without hydrogenation of the solvent. This is a critical discovery in that it enables the aforementioned recycling strategy for enhancing the GVL concentration. This then enables the easy and cost-efficient recovery of the GVL from the AP solvent by simple distillation. After distillation of GVL from the organic phase, the aqueous phase containing any residual LA and possibly acid (after extraction with the AP solvent) can be recycled for subsequent cycles of cellulose deconstruction, providing an effective strategy for managing the acid used in the deconstruction of the incoming biomass.

There are several distinct advantages to the present approach as compared to conventional approaches for making LA and GVL. Notably, APs are very effective partitioning agents for separating LA and GVL from aqueous solutions. Concomitantly, APs do not partition water or mineral acids. Thus, if an aqueous acid solution is used to deconstruct the incoming cellulose, it may be recovered entirely and recycled accordingly. The relatively high boiling point of APs allows LA and/or GVL to be distilled from the organic phase without vaporizing water. The APs are organic solvents that are inert under many upgrading reactions, such as selective hydrogenation. Because the APs have very high partition coefficients for GVL, the GVL can remain in the organic phase when LA is extracted from an aqueous solution. This allows the GVL concentration in the product stream to be increased by recycling the product stream for additional cycles of LA extraction from the aqueous phase containing LA. GVL also increases the extraction of formic acid from the aqueous reaction solution.

Another advantage is that the ultimate products (either LA or GVL) can be recovered by distillation without having to evaporate water—only the product itself is evaporated. The AP solvent does not require any further evaporation or separation, and can be directly recycled for additional extractions. Likewise the aqueous reaction solution used to deconstruct the incoming biomass can also be recycled without further purification. This solution may contain homogeneous acid catalysts, which are recovered intact after extraction.

DETAILED DESCRIPTION

Figure 1A:
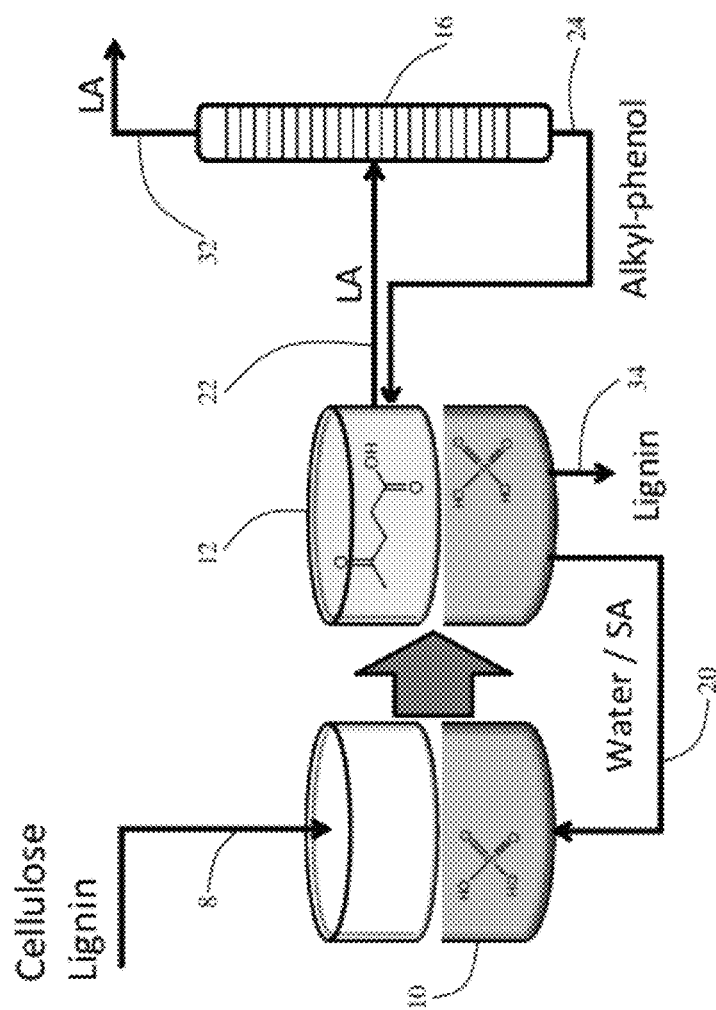
FIG. 1A is a schematic diagram depicting use of AP solvents to separate and purify LA from aqueous solutions which may contain a homogenous acid catalyst (sulfuric acid is shown).

Abbreviations and Definitions:
AP=alkylphenol. As used herein, an alkylphenol is defined as a compound having the formula:

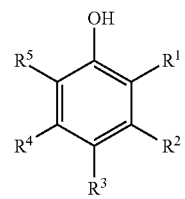

wherein R$^1$-R$^5$ are independently selected from the group consisting of hydrogen, hydroxyl, esters, ethers, carboxylic acids, and C$_1$-C$_{24}$ linear, branched, or cyclic alkyl or alkene, provided that at least one of R$^1$-R$^5$ is alkyl. All positional isomers (ortho, meta, para) are explicitly included, as are compounds having more than one hydroxy group, e.g., alkyl-substituted-1,4-dihydroxybenzene. Mono- and di-alkylphenols are preferred, as are APs wherein the alkyl substituent(s) is a $C_1$-$C_{12}$ linear, branched, or cyclic alkyl, more preferably still a $C_1$ to $C_6$ linear or branched alkyl.

BL=butyl levinulate.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

FA=formic acid. FID=flame ionization detector. GVL=γ-valerolactone. HPLC=high-performance liquid chromatography.

As used herein, the term "hydrogenation catalyst" refers without limitation to any catalyst, now known or developed in the future, homogenous or heterogeneous, that catalyzes the hydrogenation of carbonyl bonds (C=O). Preferred catalysts will reduce carbonyl bonds preferentially versus carbon-carbon double bonds (C=C). The activities need not be exclusive, but the chosen catalyst should catalyze the hydrogenation of C=O bonds at a rate much larger than the catalyst catalyzes the hydrogenation of C=C bonds. Catalysts comprising one or more metals from Groups 6-14 are preferred, also these metals doped with gallium, boron, germanium, indium and/or tin. Ruthenium, nickel, platinum copper, chromium and rhodium (alone, in combination, alloyed with other metals, and/or doped with gallium, germanium, indium and/or tin) are preferred. Other hydrogenation catalysts may also be used, such as metal hydrides (e.g., $NaBH_4$), polyoxometalates, Raney Ni, Raney Cu, etc. The catalysts may be used with or without a support.

Selective reduction may also be accomplished by transfer hydrogenation using a hydrogen donor. The term "hydrogen donor" refers to any compound with the ability to transfer a hydrogen atom to other substance. Exemplary hydrogen donors which can be utilized include, but are not limited to primary and secondary alcohols, polyols, olefins, cycloalkenes, carboxylic acids, and esters.

The rate of H-transfer can be increased by using homogeneous or heterogeneous catalysts. Exemplary catalysts include, but are not limited to, metals, zeolites, metal oxides supported or unsupported such as MgO, $ZrO_2$, gamma-$Al_2O_3$, $CeO_2$, $CeZrO_x$, $MgOAl_2O_3$, $Mg/Al/ZrO_x$, $MgO/SiO_2$, $CeO_2ZnO$, Sn-beta-zeolite, Ti-beta-zeolite, Sn-containing mesoporous silica, as well as metal salts and complexes of Pd, Pt, Ru, Ir, Rh, Fe, Ni, Co, Os, Mo. A full list of suitable hydrogen donors and catalysts can be found in R. A. W Johnsotne & A. H Wilby (1985) "Heterogeneous catalytic transfer hydrogenation and its relation to other methods for reduction of organic compounds," *Chem. Rev.* 85: 129-170, which is incorporated herein by reference.

IPA=isopropyl alcohol. LA=levulinic acid. Mineral acid=any mineral-containing acid, including (by way of example and not limitation), hydrochloric acid, nitric acid, phosphoric acid, sulfuric acid, boric acid, hydrofluoric acid, hydrobromic acid, and the like). MTHF=methyltetrahydofuran. Organic acid=any organic acid, without limitation, such as toluensulfonic acid, formic acid, acetic acid, trifluoroacetic acid, oxalic acid, and the like. SA=sulfuric acid. SBP=sec-butyl phenol.

A "solid acid catalyst" can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropoly acids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

TCD=thermal conductivity detector. WHSV=weight hour space velocity. XRD=X-ray diffraction.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Biomass to Levulinic Acid:

The inventive method to yield levulinic acid (LA) is schematically depicted in FIG. 1A. Here, a biomass feedstock 8, such as lignocellulose, cellulose, etc. is introduced into a reaction vessel 10 containing an acidic aqueous solution. The solution is preferably acidified with a mineral acid, but any acid will do, including organic or solid acids. High temperature, compressed water also demonstrates acidity and can produce LA without externally supplied acids, so long as it degrades/deconstructs the cellulose found in the feedstock 8 to yield LA. The digested, aqueous solution, which contains LA and may contain homogeneous acids, is then extracted with one or more alkylphenols (AP) in a reaction vessel 12. The AP is not soluble with the aqueous solution, so the extraction yields a biphasic system—an upper organic layer in vessel 12 (containing AP and LA) and a lower aqueous layer containing LA and any homogeneous acid used in cellulose deconstruction (sufuric acid, SA, as an exemplary embodiment in FIG. 1A) and lignin 34. Alternatively lignin and residual solids produced during deconstruction (e.g., humins) can be removed before the liquid-liquid extraction, for example, by simple filtration. As noted above, the LA partitions preferentially into the AP, while any acid, lignin and un-reacted cellulose remain in the aqueous phase. The aqueous solution can be recycled via conduit 20 into vessel 10 to be used to deconstruct additional incoming biomass.

The LA/AP solution is then transferred via conduit 22 to separator 16 where the LA is separated from the AP. The LA is removed from the separator 16 via conduit 32, while the AP is recycled from the separator 16 back into reactor 12 via conduit 24.

The separator 16 may be any separator now known or developed in the future which is dimensioned and configured to separate two or more liquids from one another. Explicitly included within the word "separator" are distillation columns of any and all description, including batch and continuous distillation columns, in any format, e.g., simple, fractional, steam, vacuum, and short-path distillation columns.

As noted in the definitions, the preferred APs for use in the method include one or two alkyl groups that are linear or branched, and generally have six or fewer carbon atoms. (Note that these are just the preferred APs; other may be used and are explicitly within the scope of the method.) LA partition coefficients and boiling points for the most preferred APs are shown in Table 1. (The values were generated using a 50/50 wt % solution of the stated AP and water containing 2M LA, 2M formic acid, and 0.5 $H_2SO_4$.)

TABLE 1

| | Partition Coeff. M/M (% of LA in org. phase) | AP Boiling Point (° C.) |
|---|---|---|
| 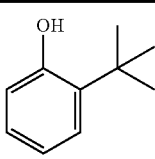 | 2.66 (82%) | 224 |

TABLE 1-continued

| | Partition Coeff. M/M (% of LA in org. phase) | AP Boiling Point (° C.) |
|---|---|---|
| 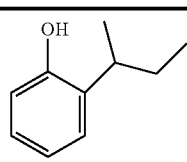 | 1.94 (78%) | 228 |
| 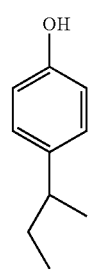 | 1.15 (70%) | 245 |
| 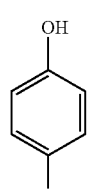 | 1.1 (70%) | 265 |
| 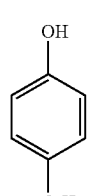 | 0.8 (60%) | 280 |
| 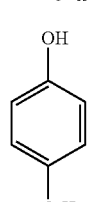 | 0.4 (40%) | 310 |
| 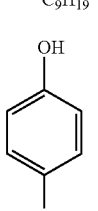 | 0.36 (30%) | 334 |

(The % value in parenthesis is the percentage of the total LA detected in the organic phase after the extraction.)

Figure 1B:
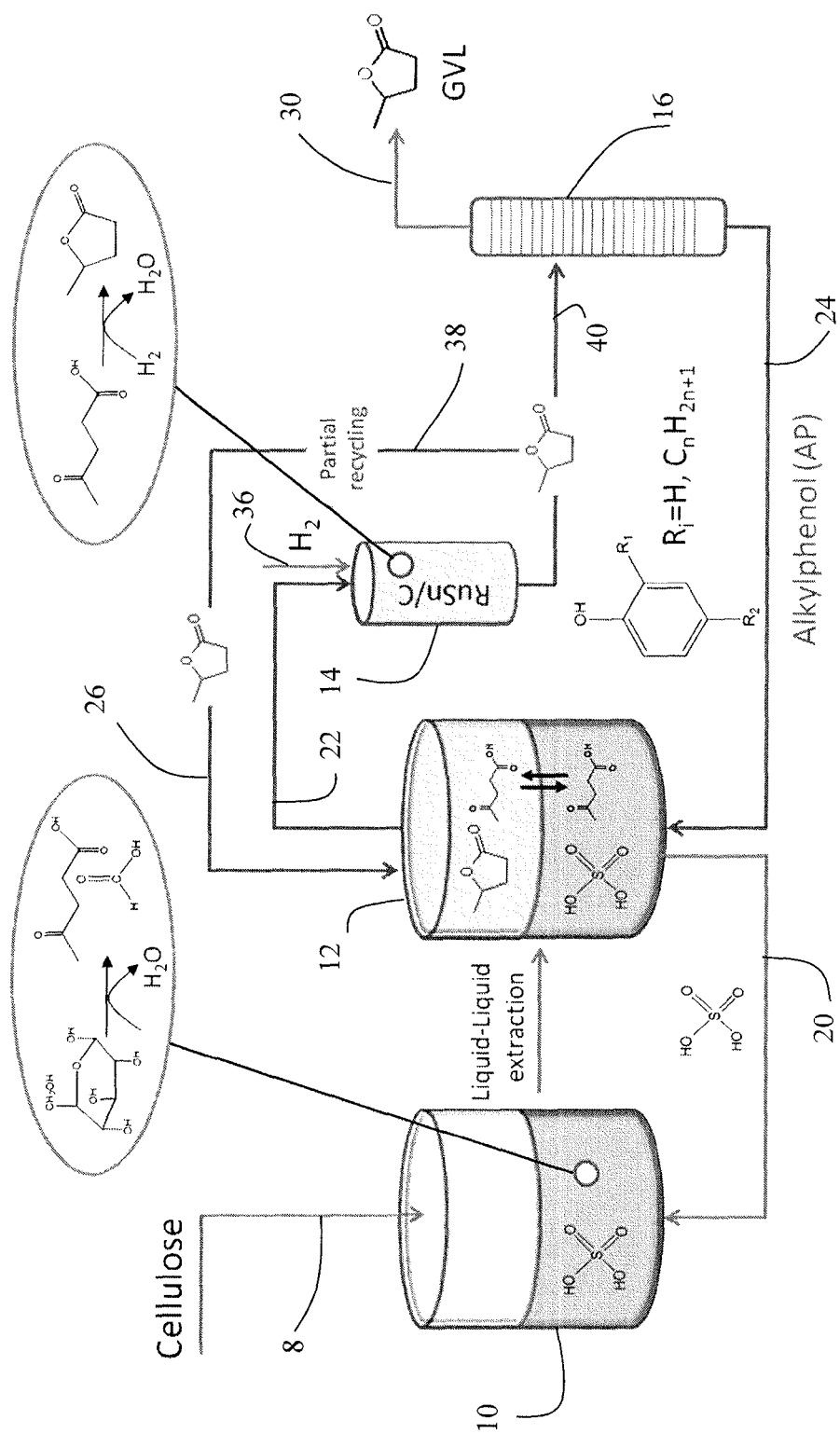
FIG. 1B is a schematic diagram depicting the use of AP solvents to produce, separate, and purify GVL from aqueous solutions of levulinic acid potentially containing homogeneous acids (sulfuric acid is shown). The process depicted can be used for deconstructing cellulose from lignocellulosic biomass.

Biomass to Gamma-Valerolactone:

FIG. 1B is a schematic illustration of another version of the method in which the LA formed as shown in FIG. 1A is further reacted (hydrogenated) over a catalyst in the presence of $H_2$ to yield GVL. In the same fashion as in FIG. 1A, in FIG. 1B a biomass feedstock 8, containing lignocellulose, cellulose, or sugars resulting from their de-polymerization is introduced into a reaction vessel 10 containing an aqueous solution.

The solution in vessel 10 degrades and deconstructs the cellulose found in the feedstock 8 to yield LA. The digested, aqueous solution containing LA is then extracted with one or more alkylphenols (AP) in a reaction vessel 12. The AP is not soluble with the aqueous reaction solution, so the extraction yields a biphasic system—an upper organic layer in vessel 12 (containing AP and LA) and a lower aqueous layer containing unreacted cellulose, any homogenous or solid acids, and lignin. The LA partitions preferentially into the AP, while any acids, lignin and any un-reacted cellulose remain in the aqueous phase. The aqueous solution can be recycled via conduit 20 into vessel 10 to be used to deconstruct additional incoming biomass.

In FIG. 1B, rather than separating the LA as a final product, the LA/AP solution is passed via conduit 22 into hydrogenation reactor 14. Hydrogen is supplied to the reactor 14 from an external source (not shown) via conduit 38 or, alternatively, the formic acid co-produced with levulinic acid can be use as internal source of hydrogen. In the reactor 14, the LA is hydrogenated to yield GVL. It is preferred that the hydrogenation reaction take place over a metallic hydrogenation catalyst, preferably a catalyst comprising ruthenium and tin on a support. See the definitions, herein, for other catalysts than can be used in the method.

At this point, the method may branch, if desired. In one version of the method, the entire bulk of the hydrogenated product exiting reactor 14, which comprises GVL may be passed directly into separator 16 via conduit 40. The GVL is removed from the separator 16 via conduit 30, while the AP is recycled from the separator 16 back into vessel 12 via conduit 24. (In the same fashion as FIG. 1A, the separator 16 may be any separator now known or developed in the future which is dimensioned and configured to separate two or more liquids from one another.)

Alternatively, the effluent from reactor 14 or a portion of the effluent from reactor 14 may be returned to vessel 12 via conduit 26. This serves to increase the concentration of GVL within the top, organic phase inside the vessel 12. This is because GVL partitions extremely favorably into the AP extracting solvent from the aqueous reaction solution used to deconstruct the biomass feed stock. For example, when the AP used for extraction in vessel 12 is sec-butylphenol, the partition coefficient for LA is 1.94 at 25° C. The partition coefficient for GVL at the same temperature is 22. Thus, the vast majority of the GVL recycled into vessel 12 via conduit 26, as well most of the newly formed LA entering vessel 12 via conduit 20 efficiently partitions into the upper, organic AP phase. By cycling the GVL through reactor 12 multiple times, the ultimate effluent passed from reactor 14 via conduit 40 into separator 16 can be greatly enriched in GVL. That makes the separation of the GVL from AP extraction solvent more efficient and economical.

More specifically, in the cellulose deconstruction step depicted in FIG. 1B, vessel 10, LA is produced in equimolar amounts with formic acid (FA) (23). Depending on the amount of cellulose added to the aqueous acidic solution, typically by stepwise addition, the LA concentration in vessel 10 can be increased to 5-10 wt % (17). An AP solvent is then added to extract LA and FA without extracting the strong acid (included in this example) in vessel 12 (sulfuric acid as shown in FIG. 1B). The data in Table 2 show that as the concentrations of LA and FA in the aqueous phase increase (entries 1-3), the partition coefficient for extraction of LA by the AP in 12 remains at a value of approximately 2 (when using 2-sec-butylphenol (SBP) as the AP), while the partition coefficient for extraction of FA increases, although remaining at low values such that most of the FA remains in the aqueous phase. Using equal masses of organic and aqueous phases, the organic phase extracts approximately 71-78% of the LA, while extracting only 2-13% of the FA. The LA partition coefficient decreases to 1.2 when using n-pentylphenol as the AP (NPP; entry 4) and to 0.8 when using n-hexylphenol as the AP (NHP; entry 5), while the FA partition coefficient does not change significantly.

TABLE 2

Partition coefficients using 4 g of aqueous phase (0.5M $H_2SO_4$) and 4 g of AP at 298 K.

| Entry | Aqueous phase (M) | | | Organic phase (g) | Total amount in organic phase (%) | | | Partition coefficient ($C_{ORG}/C_{AQ}$) | | |
|---|---|---|---|---|---|---|---|---|---|---|
| | LA | FA | GVL | AP‡ | LA | FA | GVL | LA | FA | GVL |
| 1 | 0.3 | 0.3 | — | B | 71 | 2 | — | 2.0 | 0.02 | — |
| 2 | 1 | 1 | — | B | 73 | 5 | — | 2.0 | 0.05 | — |
| 3 | 2 | 2 | — | B | 78 | 13 | — | 1.9 | 0.1 | — |
| 4 | 2 | 2 | — | P | 70 | 22 | — | 1.2 | 0.1 | — |
| 5 | 2 | 2 | — | H | 61 | 21 | — | 0.8 | 0.1 | — |
| 6 | 2* | | — | B | — | — | 96 | — | — | 22.0 |
| 7 | 2* | | — | P | — | — | 95 | — | — | 10.4 |
| 8 | 2* | | — | H | — | — | 92 | — | — | 7.8 |
| 9 | 2 | 2 | 2 | B | 61 | 23 | 93 | 0.7 | 0.1 | 6.3 |
| 10 | 2 | 2 | 4 | B | 66 | 43 | 92 | 0.6 | 0.2 | 4.0 |
| 11 | 2 | 2 | 4 | P | 68 | 55 | 89 | 0.7 | 0.4 | 2.6 |
| 12 | 2 | 2 | 4 | H | 61 | 50 | 87 | 0.5 | 0.3 | 2.3 |
| 13 | 2 | 4 | 4 | B | 68 | 50 | 92 | 0.6 | 0.3 | 3.3 |
| 14† | 2 | 2 | 4 | B | 68 | 50 | 92 | 0.6 | 0.3 | 3.5 |

*Aqueous phase is 2M GVL 0.5M $H_2SO_4$.
†at 353 K.
‡B = 2-sec-butylphenol; P = 4-n-pentylphenol; H = 4-n-hexylphenol Hydrogenation of LA to GVL leads to a decrease in the normal boiling point (from 516 to 479 K), such that GVL is more volatile than SBP (500 K), NPP (538 K), and NHP (560 K). Thus, GVL will be removed from the AP solvent at the top of the distillation column 16, eliminating the need to evaporate the solvent. As the boiling point of the AP solvent increases, the separation of GVL from the solvent requires fewer plates and lower reflux ratios (22). Furthermore, for all AP solvents investigated, the partition coefficient of GVL is higher than for LA (entries 6-8), allowing for the GVL concentration to be increased by successive recycle steps after hydrogenation, as shown in FIG. 1B. However, as the amount of GVL added in the SBP organic phase increases (entries 9 and 10), the LA partition coefficient decreases, such that the organic phase extracted 66% of the LA when a 50/50 mixture of GVL and SBP was used, as compared to 78% extraction of LA when GVL was not present (entry 3). Similar results were obtained with the other AP solvents tested (entries 11 and 12). Thus, the extent of solvent recycle prior to distillation represents a compromise between achieving high concentrations of GVL, while also maintaining a high partition coefficient for LA extraction.

Another effect of GVL being present in the organic phase in vessel 12 is that the FA partition coefficient increases slightly, but remains lower than the partition coefficient for LA and GVL, suggesting that the FA concentration in solution will increase relative to the LA concentration with repeated recycling of the aqueous solution for cellulose deconstruction. Entry 13 in Table 2 shows that a higher FA concentration does not affect the partition coefficients. In the absence of other routes for FA removal, the amounts of FA and LA extracted will become comparable, thus allowing the FA to be used as an internal source of $H_2$ for the reduction of LA to GVL (7).

Another advantage of the high boiling point of the AP solvent is that the extraction can be carried out at elevated temperatures (entry 14), suggesting that the processes presented in FIGS. 1A and 1B can be carried out at the temperatures employed for cellulose deconstruction (e.g., about 420 K), thereby decreasing the need for heat exchangers. This results in energy and equipment savings. In addition, sulfuric acid was not detected in the organic phase for any of the entries in Table 2. Thus, the aqueous phase containing 0.5 M $H_2SO_4$ can be used for multiple steps of cellulose deconstruction. After extracting the LA, the next step in the process outlined in FIG. 1B is to reduce LA to GVL. Previous literature has reported that ruthenium on carbon (Ru/C) is an effective catalyst for converting LA to GVL (10, 11); however, the Ru/C catalyst hydrogenated the C=C bonds in SBP, leading to formation of butyl-cyclohexanone (corresponding to 0.3% conversion of SBP; see Table 3, entry 1). In addition, the Ru/C catalyst undergoes deactivation with time-on-stream in the presence of FA. As shown in Table 3, the conversion of LA was only 27% and the GVL selectivity was 90.5% over the Ru/C catalyst after 100 h time-on-stream. So while this catalyst will work in the present method, it is not preferred. The LA conversion continues to decrease thereafter. Similar behavior was observed for FA, which is converted to $H_2$ and $CO_2$ (24), such that the FA conversion decreased continuously with time-on-stream (70% conversion at 100 h on-stream). Another limitation of the Ru/C catalyst is that the selectivity for conversion of FA to $CO_2$ is only 75% because of CO methanation reactions (25).

TABLE 3

Effect of temperature and feed composition on LA conversion using Ru—Sn/C with a molar ratio of 3.6:1 Ru:Sn (unless noted) in a flow reactor.

| Entry | Feed (M in SBP) LA | FA | T (K) | WHSV ($h^{-1}$) | LA conversion (%) | GVL rate (mmol $min^{-1}$ $g_{cat}^{-1}$) | LA selectivity (%) GVL | MTHF | Other |
|---|---|---|---|---|---|---|---|---|---|
| 1* | 2 | 2 | 493 | 2.8 | 27 | 0.10 | 90.5 | 0.3 | 9.2 |
| 2 | 2 | 2 | 493 | 1.5 | 46 | 0.09 | 93.4 | 4.3 | 2.3 |
| 3 | 2 | 2 | 513 | 1.2 | 58 | 0.09 | 88.5 | 5.5 | 6.0 |
| 4 | 2 | 2 | 473 | 1.2 | 19 | 0.03 | 91.0 | 1.4 | 6.8 |
| 5 | 0.5 | 0.5 | 493 | 1.2 | 54 | 0.09 | 97.7 | 0.8 | 1.5 |
| 6 | 2 | 0 | 493 | 2.2 | 98 | 0.30 | 95.8 | 3.6 | 0.6 |
| 7 | 2 | 0 | 473 | 2.2 | 52 | 0.16 | 97.5 | 2.5 | 0 |
| 8† | 2 | 2 | 493 | 1.5 | 44 | 0.09 | 92.9 | 4.6 | 2.5 |

*Catalyst 5% Ru/C.
†feed includes 2M GVL

To modify the selectivity of the catalyst to hydrogenate the C=O functional group in LA versus the C=C bonds in SBP, tin was added to the 5 wt % Ru/C in a 3.6:1 Ru:Sn molar ratio. (See the Examples.) The addition of Sn eliminated the reduction of SBP for all conditions studied in Table 3 and increased the FA selectivity (>99%) to $H_2$ (26) and $CO_2$. Furthermore, addition of Sn improved catalyst stability, such that the catalyst undergoes slow deactivation over the first 100 h, but then achieves stable performance for more than 230 h with 46% LA and greater than 90% FA conversion (Table 3, entry 2). Moreover, addition of Sn did not negatively affect the GVL production rate, and improved the GVL selectivity by minimizing formation of by-products. Increasing the temperature (entry 3) increased the LA conversion, but decreased the selectivity to GVL, such that the rate of GVL production remained constant.

Decreasing the temperature (Table 3, entry 4) decreased the rate of GVL production, with minimal effect on selectivity. Decreasing the LA and FA concentrations (entry 5) did not significantly affect the GVL production rate, indicating that the rates are of low order with respect to reactant concentrations. The rate of LA conversion is inhibited by the presence of FA, decreasing from 0.30 to 0.09 mmol $min^{-1}$ $g_{cat}^{-1}$ upon addition of FA at 493 K (entries 6 and 2), and decreasing from 0.16 to 0.03 mmol $min^{-1}$ $g_{cat}^{-1}$ at 473 K (entry 7 and 4). At both temperatures, the GVL selectivity remained high. Increasing the GVL concentration by successive recycle steps did not affect the GVL production rate. Entry 8 of Table 3 shows that 2 M GVL in the feed did not alter the GVL production rate and only slightly increased the rate of methyltetrahydrofuran (MTHF) production. Therefore, an organic solvent comprising an AP as defined herein and GVL can be used to extract LA without complications in the hydrogenation reactor.

Figure 2A:
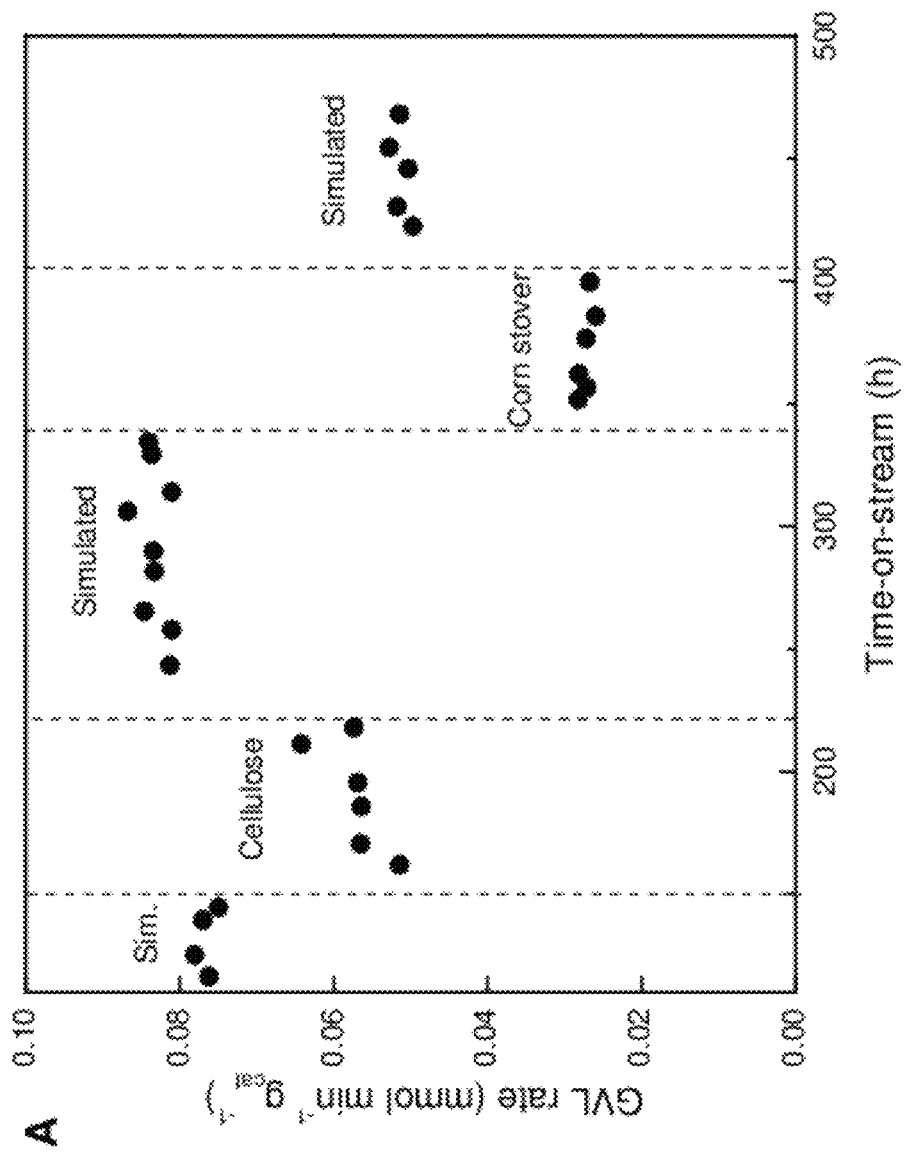
FIG. 2A is a graph depicting GVL reaction rate versus time-on-stream for different feeds of LA. Ru—Sn/C, weight hourly space velocity (WHSV)=1.2 h$^{-1}$, 493 K 35 bar (H$_2$). In the graph, simulated feed (sim.) was changed to feed prepared from cellulose, then back to simulated feed, and then switched to a feed prepared from corn stover.
Figure 2B:
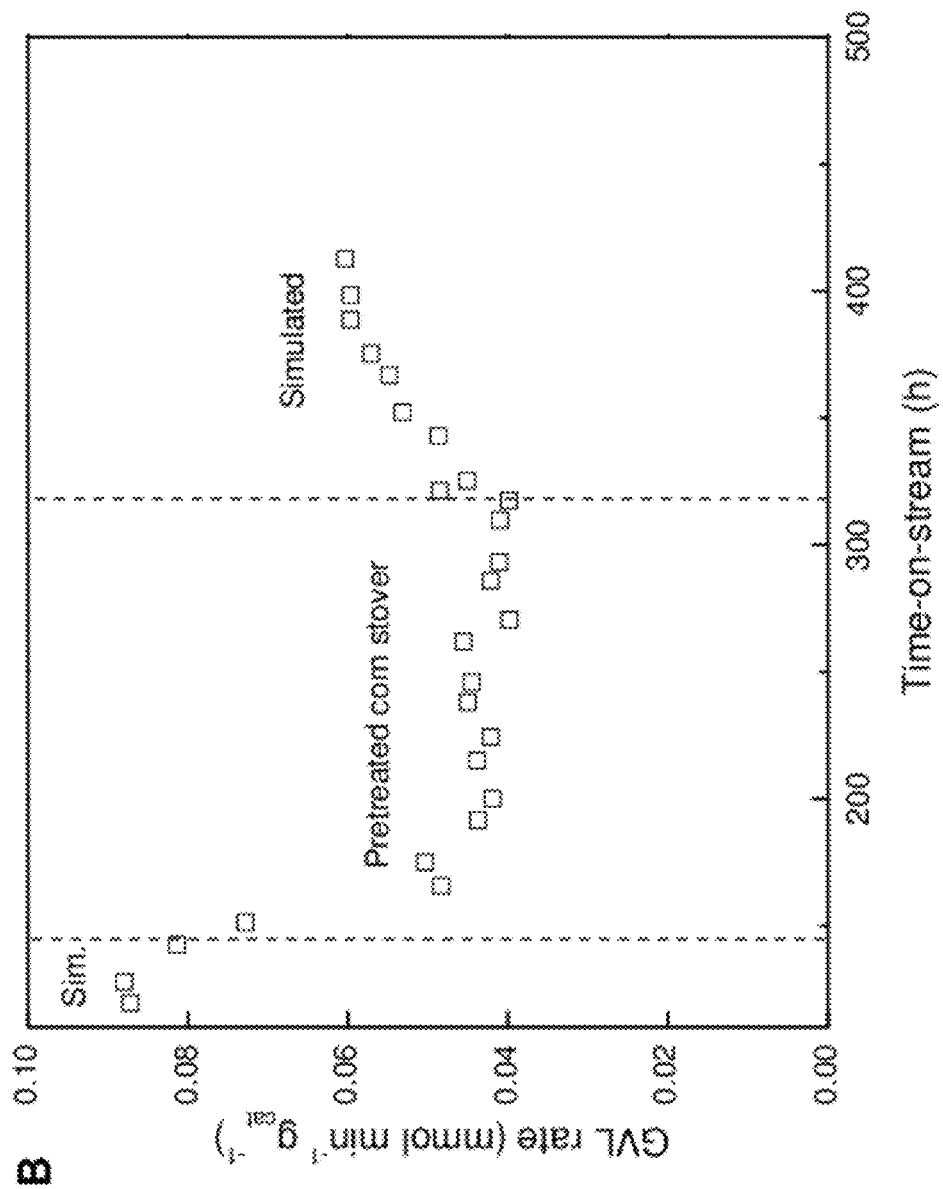
FIG. 2B is a graph depicting GVL reaction rate versus time-on-stream for different feeds of LA. The conditions were the same as described for FIG. 2A. The simulated feed was changed to a feed prepared from pre-treated corn stover, then switched back to simulated feed.

For a commercial process, impurities arising from the deconstruction of real biomass may affect the performance of the catalyst used to reduce LA to GVL. FIGS. 2A and 2B show that the rate of GVL production over the RuSn/C catalyst decreased upon changing from a simulated feed to feeds prepared by contacting SBP with aqueous solutions of LA prepared by cellulose degradation of pure cellulose (Sigma-Aldrich), untreated corn stover, and corn stover pre-treated for hemicellulose removal (22, 27). The rate of GVL production from a feed prepared from cellulose was 0.06 mmol $min^{-1}$ $g_{cat}^{-1}$, corresponding to 70% of the rate measured for the simulated feed. The catalyst recovered 100% of its activity when the feed was changed back to the simulated feed, indicating that the catalyst did not undergo irreversible deactivation during exposure to the cellulose-derived feed. At this point, the RuSn/C catalyst had been used for the production of GVL for more than 300 h (FIG. 2A).

The inlet to the hydrogenation reactor was then switched to a feed prepared from untreated corn stover and extracted with SBP, and the GVL production rate decreased to 30% of the rate measured for the simulated feed (0.03 mmol $min^{-1}$ $g_{cat}^{-1}$). Importantly, the rate of GVL formation was stable versus time on stream for this stover-derived feed (FIG. 2A), and approximately 60% of the initial activity was recovered after changing back to simulated feed. In another experiment, the simulated feed was changed to a pre-treated corn stover feed (22), and the rate of GVL production decreased to 45% of the rate of the simulated feed (0.04 mmol $min^{-1}$ $g_{cat}^{-1}$; FIG. 2B). After returning to the simulated feed, 65% of the initial activity was recovered. While it appears that impurities in the feed derived from corn stover affect catalyst performance, the pre-treatment to remove hemicellulose had little effect on the GVL production rate, indicating that the hemicellulose fraction can be separated to be processed more effectively (e.g., production of furfural and/or other $C_5$ derivatives).

As outlined in FIG. 1B, the aqueous solution of sulphuric acid and the AP solvent can be recycled to increase the concentration of GVL in the solvent. This process was simulated by conducting four recycle steps (22). The LA yield from each of the successive cellulose deconstruction steps ranged from 46-55% during the four cycles; thus showing that the aqueous solution of sulphuric acid can be recycled without further purification. The consistent yield for each of the cellulose deconstruction steps also demonstrates that the LA remaining in the aqueous phase was inert in the cellulose deconstruction reactor (17). Importantly, the AP solvent (SBP in these examples) extracted 69-75% of the LA, and 11-18% of the FA in each of the 4 cycles. The accumulating GVL did not undergo further reaction during subsequent cycles over the RuSn/C catalyst. The FA yield during cellulose deconstruction decreased from the first to subsequent cycles, suggesting that FA may undergo decomposition during this step.

The GVL concentration in the SBP solvent was 0.46 M after the first cycle of cellulose deconstruction, extraction, and hydrogenation. Upon completion of four such cycles, the GVL concentration increased to 1.44 M. For each cycle, greater than 97% of the GVL remains in the organic phase after contacting the aqueous solution from cellulose deconstruction with the solvent. The GVL that transfers into the aqueous phase remained low for each cycle (<0.03 M) and was stable during the cellulose deconstruction. In agreement with the data in Table 2, the increase in the GVL concentration in SBP with each cycle decreased the amount of LA extracted during the cycle (see Table 3). However, the effect is small and does not decrease the overall yield of LA. The cost of recycling this LA is minor compared to the decrease in the distillation column size and operating cost resulting from the overall increase in the final GVL concentration before the distillation unit (22).

The method described herein using an AP solvent offers significant advantages in the production of pure and sulfur-free GVL from biomass-derived cellulose, a required chemical to make fuels and chemicals in other downstream strategies (5, 13). The method described herein solves two important issues associated with the production of GVL from biomass: First, the process achieves effective recycle of the mineral acid catalyst used for biomass deconstruction; and second, the process achieves a high final concentration of GVL, leading to energy-efficient recovery/purification of the product (GVL).

TABLE 4

GVL concentration after successive cellulose deconstruction reactions, extractions, and hydrogenations in a batch reactor.

| Entry | Cellulose deconstruction yield (%) | | Liquid extraction amount in the organic phase (%) | | | Final product in SBP (M) |
|---|---|---|---|---|---|---|
| | LA | FA | LA | FA | GVL | GVL |
| 1 | 55 | 55 | 75 | 11 | — | 0.46 |
| 2 | 51 | 39 | 73 | 17 | 98 | 0.75 |
| 3 | 49 | 35 | 72 | 18 | 97 | 1.01 |
| 4 | 46 | 27 | 69 | 16 | 97 | 1.44 |

Any number of types of hydrogenation catalysts can be used in the method to accomplish the reduction of LA to GVL. Table 5 shows the results of hydrogenation reactions, LA to GVL, using SBP as the AP, at various reaction temperatures, and using different hydrogenation catalysts.

Figure 1C:
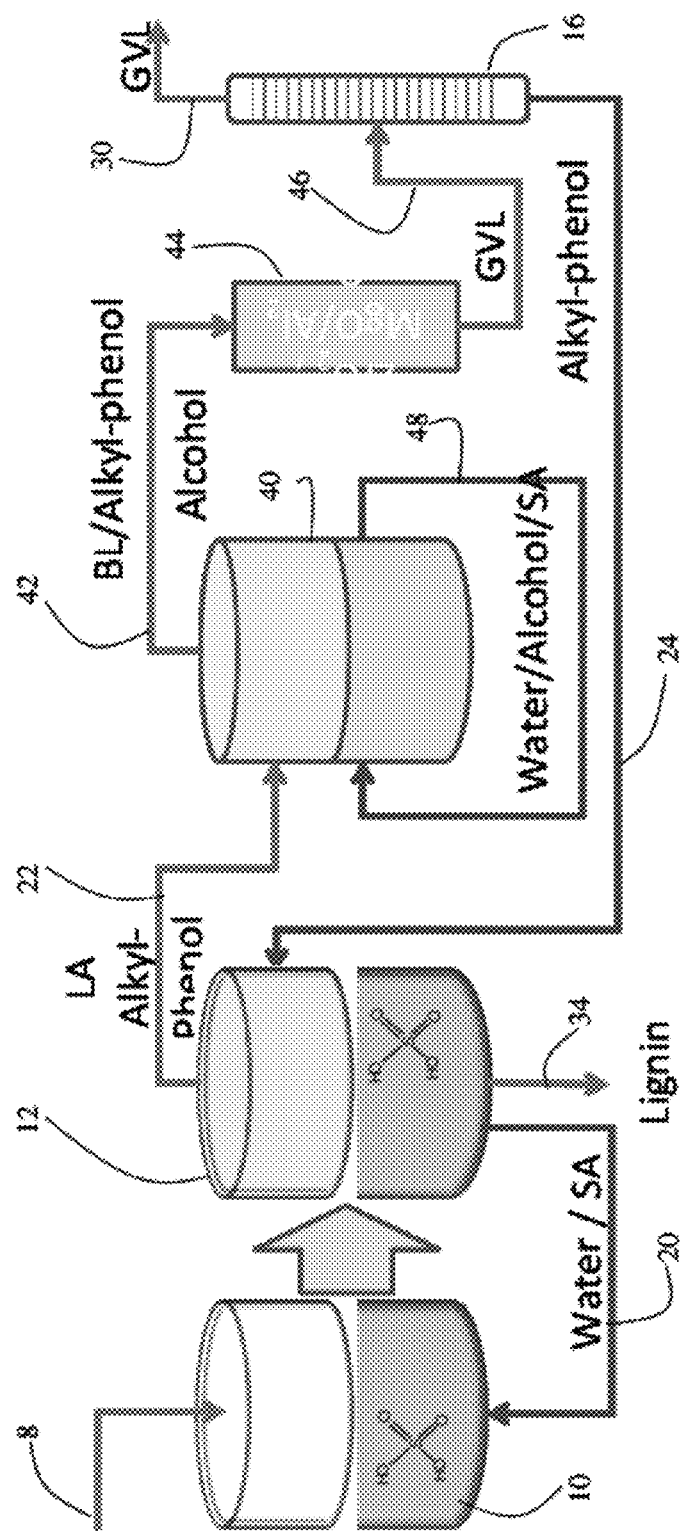
FIG. 1C is a schematic diagram depicting the conversion of LA to GVL by hydrogen transfer using butyl levinulate (BL) as the intermediate.

Another approach for converting LA to GVL is via hydrogen transfer, which is depicted schematically in FIG. 1C, where the left-hand side of the process is the same as depicted in FIG. 1A. As shown in FIG. 1C, a biomass feedstock 8 is introduced into a reaction vessel 10 containing an acidic aqueous solution. The digested, aqueous, acidic solution containing LA is then extracted with one or more alkylphenols (AP) in a reaction vessel 12. The AP is not soluble with the aqueous acidic reaction solution, so the extraction yields a biphasic system—an upper organic layer in vessel 12 (containing AP and LA) and a lower aqueous, acidic layer containing the acid (sufuric acid, SA, as an exemplary embodiment in FIG. 1C) and lignin 34. As noted above, the LA partitions preferentially into the AP, while the acid, lignin and un-reacted cellulose remain in the aqueous phase. The aqueous acid solution can be recycled via conduit 20 into vessel 10 to be used to deconstruct additional incoming biomass.

In vessel 40, the LA is esterified to produce the LA ester using an acid catalyst. Once the ester is produced, it is converted into GVL by hydrogen transfer in reactor 44, preferably using a metal oxide catalyst.

LA can be hydrogenated by hydrogen transfer using a solid oxide catalyst and a hydrogen donor such as 2-butanol. (See above for other catalysts for hydrogen transfer.) Alternatively, to increase catalyst stability and maximize yields in transfer hydrogenation, the LA can be transferred to vessel 40, to generate LA esters (i.e., levulinate esters) in the presence of alcohols or olefins. The ester can be made using homogeneous or heterogeneous catalysts. In the case of heterogeneous catalysts there will be two phases; in the case of homogeneous catalysts there will be only one phase as alcohols and olefins are soluble in AP. If the esterification of the LA is carried out using the same or a similar solution that was used for the cellulose deconstruction, the reaction results in a biphasic system in which the lower, aqueous phase in vessel 40 contains water, alcohol, and the strong acid used to produce the ester, and the upper, organic layer contains levulinate esters, alcohol, and AP. (As shown in FIG. 1C, the alcohol is 2-butanol, and thus the resulting LA ester is butyl levulinate (BL).) The water/alcohol/acid solution can be recirculated via conduit 48 for repeated esterification of levulinic acid. The upper layer containing the LA esters and AP is transferred via conduit 42 to reactor 44. Reactor 44 preferably contains a solid oxide catalyst, such as zirconia, alumina, magnesia, titania, etc. that converts the LA esters to GVL by hydrogen transfer in the presence of a hydrogen donor such as 2-butanol. (See the above for other catalysts for hydrogen trasn-

TABLE 5

Hydrogenation of LA to GVL in the presence of SBP.

| Catalyst | T (C.) | WHSV (h−1) | LA conv. (%) | GVL selectivity (%) | MTHF selectivity (%) | 1,4-pentanediol selectivity (%) | SBP hydrogenation (%) |
|---|---|---|---|---|---|---|---|
| Topsoe | 150 | 0.59 | 21 | 100 | 0 | 0 | 0 |
| Topsoe | 180 | 0.59 | 46 | 99.6 | 0.4 | 0 | 0 |
| Raney Cu | 200 | 1.13 | 95 | 99.5 | 0.1 | 0.4 | 0 |
| Raney Cu | 200 | 1.13 | 15 | 99.9 | 0.1 | 0 | 0 |
| Ru/C | 150 | 0.6 | 97 | 98.2 | 0.2 | 1.6 | 41 |
| Ru/C | 150 | 1.1 | 18 | 99.3 | 0.7 | 0 | 0.6 |
| 3.6Ru1Cu | 150 | 0.6 | 22 | 99.5 | 0.5 | 0 | 0.3 |
| 3.6Ru1Sn | 150 | 0.6 | 22 | 99.7 | 0.3 | 0 | 0 |
| 3.6Ru1Sn | 170 | 0.6 | 43 | 99.4 | 0.6 | 0 | 0 |
| 3.6Ru1Sn | 220 | 1.3 | 44 | 97.5 | 2.5 | 0 | 0 |
| 3.6Ru1Sn | 240 | 1.3 | 42 | 95.5 | 4.5 | 0 | 0 | fer.) The GVL so formed is transferred via conduit 46 to separator 16 of isolation of the LA (as described previously). As described previously, the AP may be recycled via conduit 24 into reaction vessel 12. As shown in Table 6, overall yield (LA to GVL) can be quite high using different combinations of alcohol transfer agents and APs:

TABLE 6

Hydrogen Transfer - LA Esters to GVL

| H donor | H acceptor | H donor:SBP (g:g) | Time (h) | Catalyst:ester or LA (g:g) | Ester or LA conversion (%) | GVL yield (%)* | GVL formation rate ($\mu$molg$^{-1}$min$^{-1}$) |
|---|---|---|---|---|---|---|---|
| IPA | EL | 18:1 | 16 | 1:2 | >99 | 86 | — |
| IPA | EL | 8:1 | 16 | 1:2 | >99 | 84 | — |
| IPA | EL | 1:1 | 16 | 1:2 | >99 | 95 | — |
| 2BuOH | BL | 1:1 | 16 | 1:2 | >99 | 83 | — |
| 2BuOH | BL | 1:1 | 8 | 1:5 | 60 | 51 | 27.2 |
| 2BuOH | BL | 1:1 | 4 | 1:5 | 30 | 29 | 31.5 |
| 2-HO | BL | 1:1 | 8 | 1:5 | 39 | 17 | 9.7 |
| IPA | LA | 1:4 | 16 | 1:2 | 34 | 7 | 1.3 |
| IPA | LA | 1:1 | 16 | 1:2 | 69 | 15 | 2.7 |

*Levulinate esters only by-product.
EL = ethyllevulinate,
BL = butyllevulinate,
LA = levulinic acid

EXAMPLES

The following Examples are included solely to provide a more complete disclosure of the method described and claimed herein. The Examples do not limit the scope of the claims in any fashion.

1. Materials and Methods
  1.1. Liquid-Liquid Extractions
    1.1.1. Simulated Feed Liquid-liquid extractions were carried out in 20 mL glass vials. Typically, 4 g of aqueous solution with 0.5 M sulfuric acid (Sigma-Aldrich, St. Louis, Mo., USA, >96%), LA (Sigma-Aldrich, St. Louis, Missouri, USA 98%), FA (Sigma-Aldrich, 98-100%) and/or GVL (Sigma-Aldrich, >98%), in the concentrations indicated, plus 4 g of the indicated AP (2-sec-butylphenol (Alfa Aesar, Ward Hill, Mass., USA >98%) 4-n-pentylphenol (Sigma-Aldrich, >98%), 4-n-hexylphenol (Acros Organics, Geel, Belgium, 98%) and GVL, when used, were added to the vial and shaken vigorously for one minute. After the two phases separated, the organic top phase contained SBP, GVL, LA and FA, and the aqueous bottom phase contained water, sulfuric acid, and the remaining GVL, LA and FA. Both phases were separated and weighed. The extractions at 353 K were carried out by placing the vials in an oil bath. The organic phase was analyzed by gas chromatography (Shimadzu GC2010; Shimadzu Precision Instruments, Torrance, Calif., USA) with an FID and RTx®-5-brand column (Restek Corp., Bellefonte, Pa., USA), while the aqueous phase was analyzed by HPLC (Waters 2695 system; Waters Corporation, Milford, Mass., USA) with a Bio-Rad Aminex®-brand HPX-87H column and a RI 410 detector (Bio-Rad Laboratories, Inc., Hercules, Calif., USA). Mass balances for all compounds were within 5%. The amount of FA in the organic phase was calculated by difference of the initial amount and the amount calculated in the aqueous phase.

1.1.2. Feed from cellulose deconstruction

The aqueous phase from the cellulose deconstruction reactor was mixed with an equal mass of fresh SBP in a 500 mL separatory funnel at room temperature. The mixture was shaken for 1 min and allowed to settle overnight to allow the phases to separate. For recycle experiments, the organic phase was transferred to a Parr reactor in which the hydrogenation reaction was carried out using a RuSn/C catalyst. After hydrogenation, the solution was filtered to remove the catalyst and transferred to a 500 mL separatory funnel for a subsequent extraction of the recycled aqueous phase from the cellulose deconstruction reaction. Analysis was the same as indicated in section 1.1.1.

1.2. Hydrogenation Reactions
    1.2.1. Flow Reactor

Hydrogenation of the LA was carried out in a fixed-bed reactor operating in an up-flow configuration. The catalyst was placed in a stainless steel tubular reactor (6.35 mm OD) and held between two end plugs of silica granules and quartz wool. The catalyst was reduced in-situ for 3 h at 723 K (1 K min$^{-1}$) before use. The feed was introduced into the reactor using an HPLC pump (Lab Alliance-brand Series I; Scientific System, Inc., State College, Pa., USA). Simulated feeds for catalytic experiments were prepared by adding commercial LA, FA and GVL to SBP. The flow of $H_2$ during the reaction (25 cm$^3$(STP)/min) was controlled by a mass flow controller (Brooks Instrument, 5850S; Brooks Instrument, Inc., Hatfield, Pa., USA). The tubular reactor was fitted inside an aluminum block and placed within an insulated furnace (Applied Test Systems, Butler, Pa., USA). Bed temperature was monitored at the reactor wall using a Type K thermocouple (Omega Engineering, Inc., Stamford, Conn., USA) and controlled using a 16A series programmable temperature controller (Love Controls, Inc., Michigan City, Ind., USA). Reactor pressure (35 bar of $H_2$) was controlled using a back pressure regulator (model BP-60; GO Regulator, Inc, Spartanburg, S.C., USA). The reactor effluent flowed into a vapor-liquid separator wherein the liquid product was collected. Gas phase products were analyzed using an in-line pair of gas chromatographs. A GC-2014 (Shimadzu) equipped with an FID was used for analysis of hydrocarbon products in the gas phase, while CO and $CO_2$ were quantified using a GC-8A (Shimadzu) with a TCD using helium as a carrier/reference. Liquid samples were drained from the separator and the concentration of organic species quantified using a GC-2010 (Shimadzu) with an FID. Identification of products was achieved using GC-MS analysis (Shimadzu GCQP-2010). Total and individual mass balances for each compound were within 5%.

1.2.2. Batch Reactor

A 450 mL Parr Instruments Hastelloy C-276 batch reactor (Parr Instrument Company, Moline, Ill., USA), equipped with a variable speed mechanical stirrer, was loaded with 4 g of reduced and passivated Ru—Sn/C catalyst and the organic phase coming from the liquid-liquid separation step described in section 1.1. The system was purged with helium, pressurized to 24 bar with $H_2$ and heated to 453 K (9 K $min^{-1}$ ramp) with a high-temperature fabric heating mantle to reach a final pressure of 35 bar of $H_2$. The reactor was maintained at 453 K overnight while stirring at 600 rpm. At the end of the reaction, the reactor was cooled and weighed. A liquid sample was collected, filtered with a 0.2 µm membrane (Corning, Inc., Corning, N.Y., USA), and analyzed by GC (Shimadzu GC2010 with an FID and RTx®-brand-5 column). For the recycling experiments, the organic phase was transferred to a 500 mL separatory funnel for a subsequent extraction of more LA.

1.3. Cellulose Deconstruction

1.3.1. Microcrystalline Cellulose

For the first cycle, 180 mL of 0.5 M sulfuric acid solution (Sigma-Aldrich) and 7.7 wt % microcrystalline cellulose (5% moisture, average size 20 µm, Sigma-Aldrich) were added to the 450 mL Parr reactor (section 1.2.2). The reactor was purged with helium gas three times and heated to 428 K (9 K $min^{-1}$ ramp) with a high-temperature fabric heating mantle. The reactor was maintained at 428 K for 6 h while stirring at 600 rpm. At the end of the reaction time, the heating mantle was removed, and the built-in cooling line cooled the reactor. The reactor was weighed, and another dose of cellulose (equal to the first addition) was added. The vessel was resealed and a second cycle started. After three cycles, the mixture was filtered using a 0.2 µm membrane disposable filter system (Corning), and a liquid sample was collected and analyzed by HPLC (Waters 2695 system with a Bio-Rad Aminex®-brand HPX-87H column and a RI 410 detector). The resulting concentration from three cycles was 0.68 M LA and 0.69 M FA. For the recycling process, additional degradation cycles were completed with the aqueous solution remaining from the previous separation step.

1.3.2. Corn Stover

Dried corn stover was obtained through the Great Lakes Bioenergy Research Center, Madison, Wis., USA. Approximately 20 g of dry corn stover and 270 mL of 0.5 M sulfuric acid, which results in an approximately 2.5 wt % cellulose solution, were added to the 450 mL Parr reactor (section 1.2.2). The corn stover was then deconstructed and analyzed as indicated in section 1.3.1. The resulting concentration after three cycles was 0.25 M LA and 0.37 M FA.

1.3.3. Pretreated Corn Stover

A 5 to 5.5 wt % solids mixture of corn stover and 0.05 M sulfuric acid was added to the 450 mL Parr reactor in accord with previously published methods (24). The reactor was purged 3 times with helium, heated to 433 K in 20 min, and held at 433 K for an additional 20 min. The reactor was cooled using an inline water cooling line and blowing air. The reactor was weighed, the contents filtered, and the aqueous phase analyzed by HPLC (Waters 2695 system with a Bio-Rad Aminex®-brand HPX-87H column and a RI 410 detector). The remaining solids were dried overnight in a 358 K oven. The solids were then used as the cellulose source for deconstruction as in section 1.3.1. The resulting concentration from three cellulose deconstruction cycles using the pretreated corn stover was 0.50 M LA and 0.54 M FA.

1.4. Catalysts

1.4.1. Synthesis

The 5 wt % Ru/C was used as received from the vendor (Sigma-Aldrich). The Ru—Sn/C catalyst was prepared by incipient wetness impregnation of the 5 wt % Ru/C catalyst with a solution of $SnCl_2.2H_2O$, which resulted in a final molar ratio Ru:Sn of 3.6:1. The catalyst was dried at 353 K for 2 hours before loading into a flow reactor, or reduced for 3 h at 723 K (1 K $min^{-1}$) and passivated in 2% $O_2$/He for 3 hours before use in a batch reactor.

1.4.2. Chemisorption

Fresh and spent RuSn/C samples were characterized by volumetric titration of exposed metal sites with carbon monoxide. Static chemisorption was carried out using a Micromeritics ASAP 2020 (Micromerimetrics Instrument Corp., Norcross, Ga., USA). Prior to analysis, catalyst samples were outgassed under vacuum at 303 K and subsequently reduced in flowing $H_2$ at 723 K (80 $cm^3$(STP)/min $H_2$, 1.3 K $min^{-1}$ heating rate, 240-min hold). The sample was then evacuated at 723 K for 60 min to remove adsorbed $H_2$ and cooled to 303 K. CO uptake was measured volumetrically at 303 K through sequential doses at incrementing pressures to approximately 10 Torr. The sample was again evacuated at 303 K, and a second CO uptake isotherm was collected. Irreversible adsorption of CO was taken as the difference in uptake between the two isotherms, and dispersions were calculated by normalizing total CO uptake by total metal content (Ru plus Sn).

1.4.3. X-ray Diffraction

X-Ray diffraction (XRD) was used to probe the extent of interaction between Ru and Sn on the carbon support. In addition, XRD studies provided information regarding metal particle size of fresh and spent catalysts. Powder diffraction was carried out using a Rigaku Rapid II large area curved imaging plate detector (Rigaku Americas, Inc., The Woodlands, Tex., USA) with a molybdenum source. Prior to XRD studies, RuSn/C catalysts were prepared according to the methods described in section 1.4.1, reduced in flowing $H_2$ at 723 K (50 $cm^3$(STP)/min $H_2$, 1.3 K $min^{-1}$ heating rate, 4 h hold), and subsequently passivated at 298 K under $O_2$/He flow (50 $cm^3$(STP)/min, 2% $O_2$ in He). Samples were crushed to a uniform particle size and loaded into a 0.5 mm borosilicate capillary for analysis.

2. RuSn/C Catalyst

2.1. Stability

Figure 3:
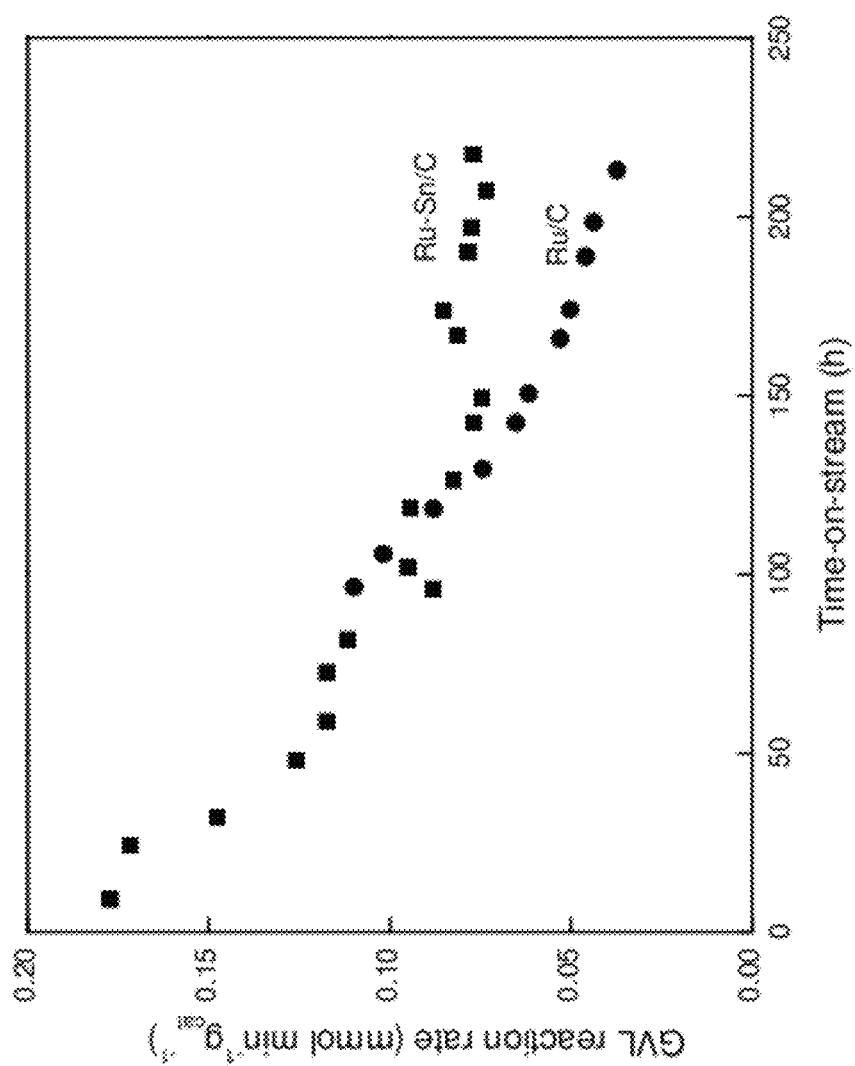
FIG. 3 is a graph depicting GVL production rate versus time on stream at 493 K and 35 bar (H$_2$). Feed composition is 2 M LA and 2 M FA in SBP with a WHSV of 1.6 h$^{-1}$ for Ru—Sn/C (■) and 2.9 h$^{-1}$ for Ru/C (●).
Figure 4:
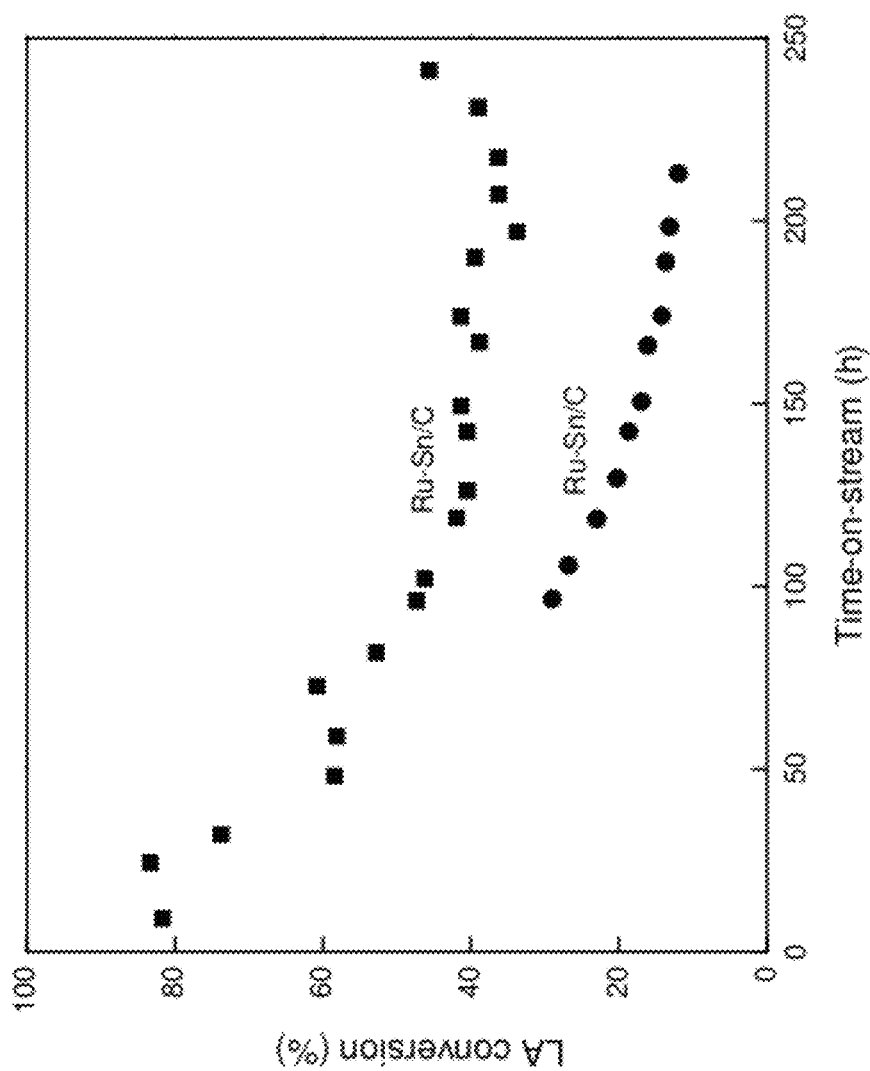
FIG. 4 is a graph depicting LA conversion versus time on stream at 493 K and 35 bar (H$_2$). Feed composition is 2 M LA and 2 M FA in SBP with a WHSV of 1.6 $^{-1}$ for Ru—Sn/C (■) and 2.9 h$^{-1}$ for Ru/C (●).

FIGS. 3 and 4 illustrate that the Ru—Sn/C catalyst initially undergoes deactivation, during which the rate of GVL production and LA conversion decrease in the first 100 h on stream. The catalyst then remains stable for more than 200 h. In the case of Ru/C, the catalyst showed continuous deactivation, with the rates of GVL production and LA conversion decreasing continuously after 200 h.

2.2. Characterization

In XRD patterns for both fresh and spent RuSn/C, the only observable signal was attributed to the carbon support. XRD did not reveal the presence of phases corresponding to metallic Ru, metallic Sn, or $Ru_xSn_y$ alloys. The absence of signal arising from distinct metal or alloy phases suggests that the metal nanoparticles are highly dispersed (<4 nm) in both fresh and spent samples.

The fresh RuSn/C irreversibly adsorbs 101 µmol-CO $g^{-1}$, corresponding to a metal dispersion of approximately 16%, which is lower than that observed for the original Ru/C (26% dispersion). This result is consistent with expectations that CO does not adsorb irreversibly on metallic tin. The CO uptake decreases by nearly an order of magnitude to 12 µmol $g^{-1}$ for the spent RuSn/C catalyst, with an apparent dispersion of 1.9%. A decrease in CO uptake and observed dispersion may be attributed to metal sintering and an increase in average particle size; however, this explanation is not consistent with XRD results, which showed that significant growth of the metal particles does not take place upon exposure to reaction conditions. Thus, the reduced CO adsorption capacity may be attributed to deposition of carbonaceous deposits on the metal particles and/or enrichment in the surface of the metal particles with Sn.

3. Stream Recycle Results 3.1. Cellulose Deconstruction

Data for successive cellulose deconstruction reactions can be found in Table 7.

TABLE 7

Initial and final concentrations of LA, FA and GVL and LA and FA yields, resulting from successive cellulose deconstruction reactions using recycled SA.

| Entry | Initial concentration (M) | | | Final concentration (M) | | | Yield (%) | |
|---|---|---|---|---|---|---|---|---|
| | LA | FA | GVL | LA | FA | GVL | LA | FA |
| 1 | — | — | — | 0.68 | 0.69 | 0 | 55 | 55 |
| 2 | 0.19 | 0.70 | — | 0.83 | 1.19 | 0 | 51 | 39 |
| 3 | 0.26 | 1.11 | <0.05 | 0.87 | 1.55 | <0.05 | 49 | 35 |
| 4 | 0.34 | 1.39 | <0.05 | 0.92 | 1.73 | <0.05 | 46 | 27 |

As the number of times the aqueous solution was recycled increased, the initial concentration of LA and FA increased. At higher FA concentrations, the FA decomposed into $CO_2$ and $H_2$, which were detected using a GC-8A (Shimadzu) with a TCD using helium as a carrier/reference.

3.2. Extraction

After extraction, the organic phase was transferred to a Parr reactor for hydrogenation of LA and the aqueous phase containing SA was recycled for a second cellulose deconstruction. In subsequent cycles, the aqueous phase coming from the cellulose deconstruction reactor was mixed with the organic phase from the previous hydrogenation step. Therefore, after the first hydrogenation step, GVL is present in both the aqueous and organic streams. Aqueous and organic phases were analyzed as mentioned in section 1.1. Detailed data for these extractions can be found in Table 8.

TABLE 8

Aqueous and organic phase concentrations and percentages of LA, FA and GVL before and after extraction with SBP.

| | Initial aqueous phase | | | Organic phase | | | | | | | Final aqueous phase | | | | | |
|---|---|---|---|---|---|---|---|---|---|---|---|---|---|---|---|---|
| | | | | Initial | Final | | Final | | Final | | LA | | FA | | GVL | |
| | LA | FA | GVL | GVL | LA | | FA | | GVL | | | | | | | |
| Entry | (M) | (M) | (M) | (M) | (M) | (%) | (M) | (%) | (M) | (%) | (M) | (%) | (M) | (%) | (M) | (%) |
| 1 | 0.68 | 0.69 | 0 | 0 | 0.42 | 74.1 | 0.07 | 11.4 | 0 | 0 | 0.19 | 25.9 | 0.70 | 88.6 | 0 | 0 |
| 2 | 0.83 | 1.19 | 0 | 0.46 | 0.46 | 72.2 | 0.15 | 16.8 | 0.42 | 97.8 | 0.26 | 27.8 | 1.11 | 83.2 | 0.01 | 2.2 |
| 3 | 0.87 | 1.55 | 0.02 | 0.75 | 0.56 | 71.5 | 0.22 | 20.2 | 0.66 | 97.5 | 0.34 | 28.5 | 1.39 | 79.8 | 0.03 | 2.5 |
| 4 | 0.92 | 1.73 | 0.03 | 1.04 | 0.52 | 69.4 | 0.17 | 15.8 | 0.96 | 96.6 | 0.40 | 30.6 | 1.60 | 84.2 | 0.06 | 3.4 |

3.3. Hydrogenation of LA

Detailed results for the successive batch hydrogenation reactions of LA can be found in Table 9. For each batch, fresh catalyst was used (4 g). At these high reaction times (i.e., overnight) using fresh catalyst, some reduction of the SBP was observed. However, the GVL selectivity remained over 97% in all cases.

TABLE 9

LA conversion and selectivities for successive hydrogenation reactions using RuSn/C at 453 K and 35 bar ($H_2$) overnight.

| | Initial (M) | | Final (M) | | LA conversion | Selectivity (%) | | SBP hydrogenation |
|---|---|---|---|---|---|---|---|---|
| Entry | LA | GVL | LA | GVL | (%) | GVL | MTHF | (%) |
| 1 | 0.42 | 0 | 0 | 0.46 | 100 | 97.0 | 2.6 | 0.8 |
| 2 | 0.46 | 0.42 | 0.15 | 0.75 | 67.4 | 97.0 | 2.0 | 0.4 |
| 3 | 0.56 | 0.66 | 0.14 | 1.01 | 74.8 | 98.6 | 1.2 | 1.5 |
| 4 | 0.52 | 0.96 | 0.02 | 1.44 | 96.2 | 97.9 | 2.1 | 1.4 |

4. Distillation

Figure 5:
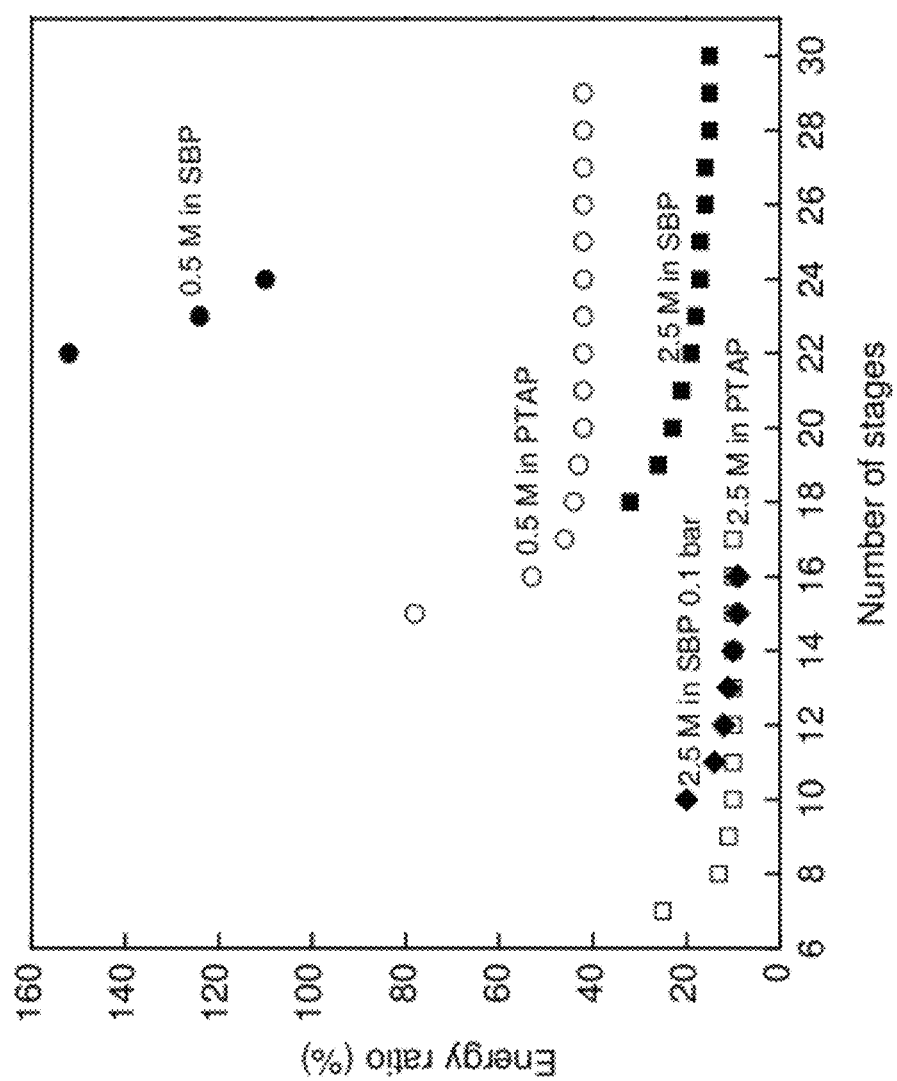
FIG. 5: Energy ratio (defined as percentage of GVL low combustion energy) used in the reboiler versus the number of stages in the separation by distillation of GVL from AP at 1 bar. Feed concentration of GVL: 2.5 M in SBP (■), 0.5 M in SBP (●), 2.5 M in PTAP (□), 0.5 M GVL in PTAP (○), and 2.5 M in SBP at 0.1 bar (◆).

In the final step of the process, GVL is separated from the AP, obtaining pure GVL at the top of a distillation column. ASPEN PLUS®-brand modeling software (Aspen Technology, Inc., Burlington, Mass., USA) was used to conduct simulations of the distillation column using different feed compositions and alkylphenols. FIG. 5 shows the energy ratio (heat necessary in the reboiler divided by the lower combustion heat of GVL) as indicative of the operational cost, versus the number of stages, as indicative of the capital cost, to recover 95% of the GVL with 95 wt % purity from the feed at 298 K and 1 bar.

Increasing the concentration of GVL in the feed from 0.5 M to 2.5 M considerably reduces the number of stages necessary to achieve separation and the heat required in the reboiler. For example, using 0.5 M GVL in SBP as feed and with 22 stages, the energy ratio is 152%, meaning that 52% more energy is required than is provided by the combustion of the GVL. When the GVL feed concentration is 2.5 M, then the energy ratio is only 19%, and 10 stages are required. Similar reductions in reboiler energy requirements are observed using AP solvents with higher boiling points. For example, the energy ratio is 10% using para-tert-amylphenol (PTAP) as the solvent, a GVL concentration of 2.5 M, and 10 stages. Another option to reduce the reboiler heat and the number of stages is to carry out the distillation under vacuum (0.1 bar), but such operation increases capital and operating costs.

Figure 6:
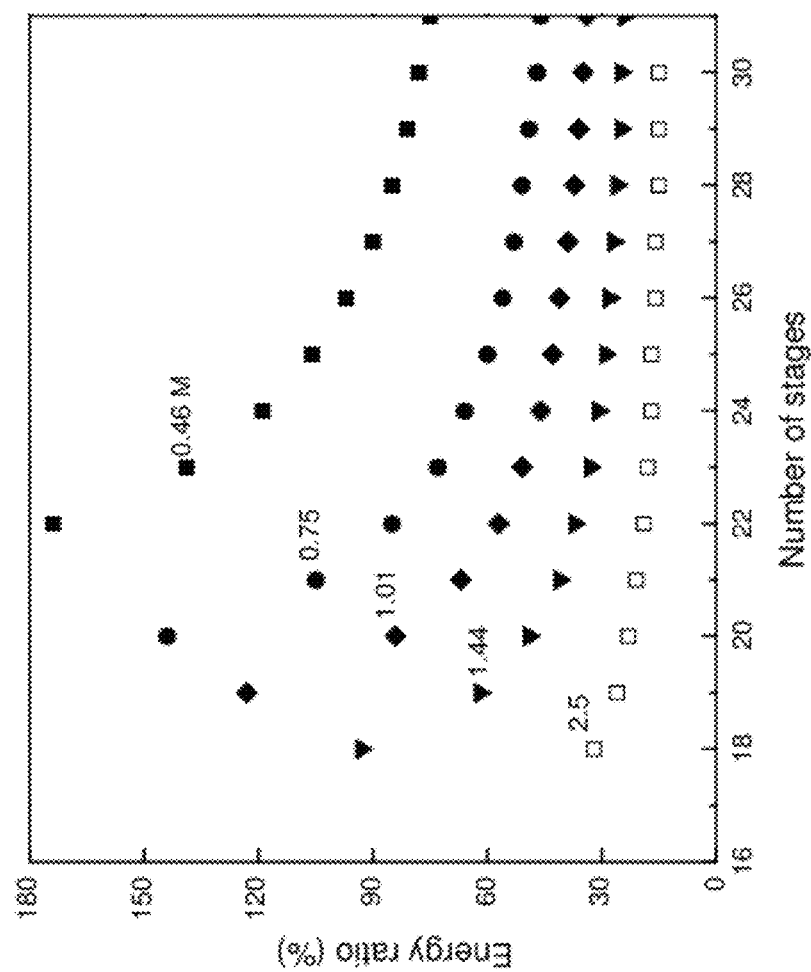
FIG. 6: Energy ratio (defined as percentage of GVL low combustion energy) versus number of stages in the separation by distillation of GVL from AP at 1 bar. Feed composition of GVL into distillation column: 0.46 M in SBP (■), 0.75 M in SBP (●), 1.01 M in SBP (◆), 1.44 M in SBP (▼), and 2.5 M in SBP (□).

FIG. 6 shows the simulated decrease in required reboiler heat and number of stages associated with the deconstruction/extraction/hydrogenation recycling steps documented herein, illustrating how the size of the column and the energy requirements decrease as the GVL concentration increases. For example, after a single cycle, the GVL concentration is 0.44 M and 30 stages are necessary to carry out the separation, with an energy ratio of 78%. After 4 cycles, the GVL concentration has increased to 1.44 M, and with the same number of stages, the energy ratio is just 25%. Additional increases in GVL concentration further reduce the heat requirements and size of the column. Additional energy saving can be achieved if the distillation column is fed directly from the hydrogenation reactor at 493 K, alleviating the need to heat the stream prior to distillation.

REFERENCES

1. E. L. Kunkes et al., *Science* 322, 417 (2008).
2. D. M. Alonso, J. Q. Bond, J. A. Dumesic, *Green Chem.* 12, 1493 (2010).
3. J. J. Bozell, G. R. Petersen, *Green Chem.* 12, 539 (2010).
4. J. J. Bozell, *Science* 329, 522 (2010).
5. J. P. Lange et al., *Angew. Chem. Inter. Ed.* 49, 4479 (2010).
6. F. M. A. Geilen et al., *Angew. Chem. Inter. Ed.* 49, 5510 (2010).
7. H. Heeres et al., *Green Chem.* 11, 1247 (2009).
8. H. Mehdi et al., *Top. Catal.* 48, 49 (2008).
9. J. J. Bozell et al., *Resour. Conserv. Recy.* 28, 227 (2000).
10. L. Deng, J. Li, D. M. Lai, Y. Fu, Q. X. Guo, *Angew. Chem. Int. Ed.* 48, 6529 (2009).
11. Z. P. Yan, L. Lin, S. J. Liu, *Energ. fuel* 23, 3853 (2009).
12. I. T. Horvath, H. Mehdi, V. Fabos, L. Boda, L. T. Mika, *Green Chem.* 10, 238 (2008).
13. J. Q. Bond, D. M. Alonso, D. Wang, R. M. West, J. A. Dumesic, *Science* 327, 1110 (2010).
14. J. P. Lange, J. Z. Vestering, R. J. Haan, *Chem. Commun.*, 3488 (2007).
15. D. Fegyverneki, L. Orha, G. Lang, I. T. Horvath, *Tetrahedron* 66, 1078 (2010).
16. S. W. Fitzpatrick. U.S. Pat. No. 5,608,105 (1997).
17. J. C. Serrano-Ruiz, D. J. Braden, R. M. West, J. A. Dumesic, *Appl. Catal. B-Environ.* 100, 184 (2010).
18. D. J. Braden, thesis, UW-Madison (2010).
19. Kirk-Othmer Encyclopedia of Chemical Technology (Ed Wiley, New York 2000) vol. 2, pp. 203-232.
20. B. A. Riguetto et al., *Appl. Catal. Gen.* 318, 70 (2007).
21. J. Springerova, P. Kacer, L. Cerveny, *Res. Chem. Intermediat.* 31, 785 (2005).
22. See Examples and figures.
23. J. Horvat, B. Klaic, B. Metelko, V. Sunjic, *Tetrahedron Lett.* 26, 2111 (1985).
24. C. Fellay, P. J. Dyson, G. Laurenczy, *Angew. Chem. Int. Edit.* 47, 3966 (2008).
25. M. R. Prairie, A. Renken, J. G. Highfield, K. R. Thampi, M. Gratzel, *J. Catal.* 129, 130 (1991).
26. G. W. Huber, J. W. Shabaker, J. A. Dumesic, *Science* 300, 2075 (2003).
27. C. G. Liu, C. E. Wyman, *Ind. Eng. Chem. Resear.* 42, 5409 (2003).

What is claimed is:

1. A method to isolate levulinic acid (LA), the method comprising:
    (a) providing an aqueous solution of LA; and
    (b) extracting the LA from the aqueous solution of step (a) using an extraction solvent comprising at least one alkylphenol (AP).

2. The method of claim 1, comprising in step (a) providing an acidic, aqueous solution of LA.

3. The method of claim 2, wherein the acidic, aqueous solution comprises an acid selected from the group consisting of solid acids, hydrochloric acid, nitric acid, phosphoric acid, sulfuric acid, boric acid, hydrofluoric acid, trifluoroacetic acid, hydrobromic acid, acetic acid, oxalic acid, and toluenesulfonic acid.

4. The method of claim 1, wherein the LA is extracted from the aqueous solution of step (a) using at least one AP selected from the group consisting of

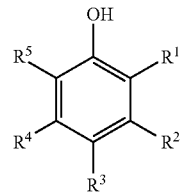

wherein $R^1$-$R^5$ are independently selected from the group consisting of hydrogen, hydroxyl, esters, ethers, carboxylic acids, and $C_1$-$C_{24}$ linear, branched, or cyclic alkyl or alkene, provided that at least one of $R^1$-$R^5$ is alkyl.

5. The method of claim 4, wherein $R^1$-$R^5$ are independently selected from the group consisting of hydrogen, hydroxyl, and $C_1$-$C_{12}$ linear, branched, or cyclic alkyl, provided that at least one of $R^1$-$R^5$ is alkyl.

6. The method of claim 4, wherein $R^1$-$R^5$ are independently selected from the group consisting of hydrogen, hydroxyl, and $C_1$-$C_6$ linear or branched alkyl, provided that at least one of $R^1$-$R^5$ is alkyl.

7. The method of claim 1, further comprising, after step (b):
    (c) separating the extracted LA from the AP.

8. The method of claim 7, wherein the LA is separated from the AP by distillation.

9. The method of claim 1, further comprising, after step (b):
    (c) hydrogenating the LA into GVL.

10. The method of claim 9, wherein step (c) comprises hydrogenating the LA into GVL in the presence of a catalyst comprising one or more metals from Groups 6-14 of the periodic chart.

11. The method of claim 9, wherein step (c) comprises hydrogenating the LA into GVL in the presence of a catalyst comprising ruthenium, nickel, platinum, rhodium, tin, copper, and combinations thereof.

12. The method of claim 11, wherein the catalyst comprises ruthenium and tin.

13. The method of claim 9, wherein step (c) comprises hydrogenating the LA into GVL by converting the LA into a LA ester and reducing the LA ester to GVL.

14. The method of claim 13, wherein the LA ester is reduced to GVL in the presence of a metal oxide or metal complex catalyst.

15. A method to make γ-valerolactone (GVL), the method comprising:
    (a) deconstructing biomass in an aqueous acidic solution to yield LA;
    (b) extracting the LA from the aqueous acidic solution of step (a) using an extraction solvent comprising at least one alkylphenol (AP); and
    (c) hydrogenating the LA into GVL.

16. The method of claim 15, wherein the aqueous acidic solution in step (a) comprises a mineral acid.

17. The method of claim 16, wherein the mineral acid is selected from the group consisting of hydrochloric acid, nitric acid, phosphoric acid, sulfuric acid, boric acid, hydrofluoric acid, and hydrobromic acid.

18. The method of claim 15, wherein the LA is extracted from the aqueous acidic solution of step (a) using at least one AP selected from the group consisting of

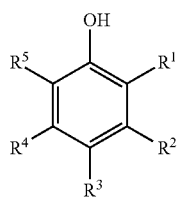

wherein $R^1$-$R^5$ are independently selected from the group consisting of hydrogen, hydroxyl, and $C_1$-$C_{24}$ linear, branched, or cyclic alkyl, provided that at least one of $R^1$-$R^5$ is alkyl.

19. The method of claim 18, wherein $R^1$-$R^5$ are independently selected from the group consisting of hydrogen, hydroxyl, and $C_1$-$C_{12}$ linear, branched, or cyclic alkyl, provided that at least one of $R^1$-$R^5$ is alkyl.

20. The method of claim 18, wherein $R^1$-$R^5$ are independently selected from the group consisting of hydrogen, hydroxyl, and $C_1$-$C_6$ linear or branched alkyl, provided that at least one of $R^1$-$R^5$ is alkyl.

21. The method of claim 15, wherein step (c) comprises hydrogenating the LA into GVL in the presence of a catalyst comprising one or more metals from Groups 9-12 of the periodic chart.

22. The method of claim 15, wherein step (c) comprises hydrogenating the LA into GVL in the presence of a catalyst comprising ruthenium, nickel, platinum, rhodium, tin, copper, and combinations thereof.

23. The method of claim 22, wherein the catalyst comprises ruthenium and tin.

24. The method of claim 15, wherein step (c) comprises hydrogenating the LA into GVL by converting the LA into a LA ester and reducing the LA ester to GVL.

25. The method of claim 24, wherein the LA ester is reduced to GVL in the presence of a metal oxides or metal complex catalyst.

* * * * *